United States Patent [19]

Evans

[11] Patent Number: 4,510,133
[45] Date of Patent: Apr. 9, 1985

[54] METHOD FOR COMBATING PESTS

[75] Inventor: David D. Evans, Finchampstead, England

[73] Assignee: Imperial Chemical Industries PLC, London, England

[21] Appl. No.: 479,915

[22] Filed: Mar. 28, 1983

[30] Foreign Application Priority Data

Apr. 22, 1982 [GB] United Kingdom ................ 8211706

[51] Int. Cl.³ .............................................. A61K 31/71
[52] U.S. Cl. ........................................ 514/30; 536/7.1
[58] Field of Search .......................... 424/180; 536/7.1

[56] References Cited

U.S. PATENT DOCUMENTS

| | | | |
|---|---|---|---|
| 4,156,720 | 5/1979 | Fisher et al. | 536/7.1 |
| 4,199,569 | 4/1980 | Chabala et al. | 536/7.1 |
| 4,203,976 | 5/1980 | Fisher et al. | 536/7.1 |
| 4,289,760 | 9/1981 | Mrozik et al. | 536/7.1 |
| 4,333,925 | 6/1982 | Buhs et al. | 536/7.1 |

*Primary Examiner*—Johnnie R. Brown
*Attorney, Agent, or Firm*—Cushman, Darby & Cushman

[57] ABSTRACT

Insecticidally active compositions comprising a combination of a C-076 or B-41 macrolide antibiotic with an insect feeding stimulant. The combination shows substantially enhanced activity compared with combinations of pyrethroid insecticides with feeding stimulants.

5 Claims, No Drawings

METHOD FOR COMBATING PESTS

This invention relates to a composition and method for combating insect, acarine and like pests of plants.

It is known to combat insect and like pests of plants by the use of compositions comprising known insecticides in admixture with certain additives which enhance the activity of the insecticides. In particular it is known that certain materials having an insect feeding stimulant effect can enhance the activity of certain insecticides. Thus pyrethroid insecticides, such as, for example, permethrin or cypermethrin can be made more effective in the control of cotton pests such as Heliothis species by spraying in admixture with the insect feeding stimulant sold under the name "COAX" and manufactured by the Traders Protein Division of the Traders Oil Mill Company of Fort Worth, Tex., U.S.A. "COAX" consists of a mixture of materials described as specially prepared "Pharmamedia" (registered trade mark) cottonseed flour, fisaccharide, vegetable lipid oil and ethoxylated ester.

We have now discovered that certain insecticidally active macrolide antibiotic substances can be made substantially more effective by applying them in conjunction with an insect feeding stimulant. The enhancement of activity in this case is substantially greater than would be expected from the level of enhancement obtained with pyrethroid insecticides.

Accordingly the present invention provides an insecticidal composition comprising a macrolide antibiotic substance selected from the groups consisting of B-41 and C-076 antibiotics and their simple derivatives (including acylated derivatives, aglycones and the like) in association with an insect feeding stimulant. The invention further provides a method of combating insect, acarine and like pests of growing plants which comprises applying the invention compositions to the plants.

C-076 and B-41 macrolide antibiotic substances and their derivatives (hereinafter called the active ingredients) are fully described in the following patents (the disclosures of which are herein incorporated by reference) viz. U.S. Pat. Nos. 3,998,699, 3,992,527, 3,992,551, 3,992,552, 3,984,564, 3,950,360, 4,134,973, 4,093,629, 4,199,569, 4,206,205, 4,201,861, 4,171,314 and 4,203,976, British Pat. Nos. 1573955 and 1390336 and published European Patent Application No. 0008184. Such C-076 antibiotics are also known as avermectins and B-41 antibiotics are also known as milbemycins. Particular examples of C-076 antibiotics useful in the invention compositions and methods include that known as Avermectin $B_1a$, the structure of which is given by Chabala et al, J. Agric. Food Chem. 1981, 19, 881–884 at 885, and that known as Ivermectin which is the 22,23-dihydro derivative of Avermectin $B_1a$ and has the structure:

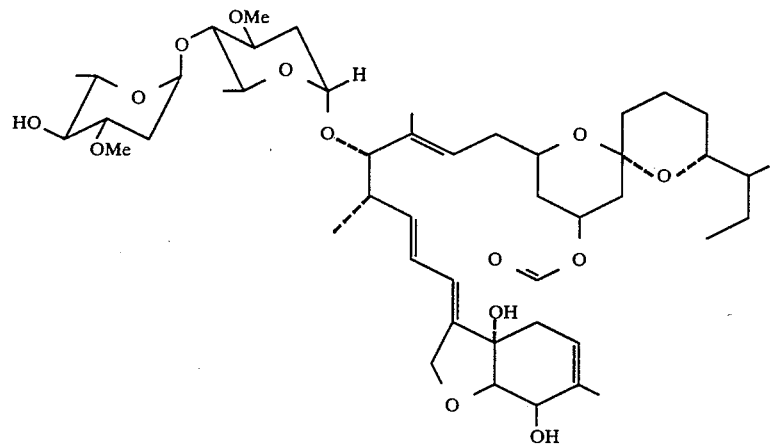

A particular useful insect feeding stimulant substance is one containing one or more of cottonseed flour, disaccharide, and vegetable lipid oil, for example that sold under the name "COAX" referred to hereinabove.

The compositions of the invention may be prepared as concentrates and diluted before use but a more convenient method is to prepare a tank mix in which the feeding stimulant is dispersed in water and thereafter the active ingredient is added with further agitation just prior to spray application onto the crop to be protected.

The application rate with respect to the feeding stimulant is preferably in the range 1 to 10 lbs/acre (ca. 1 to 10 kg/ha) and the application rate with respect to the macrolide antibiotic is preferably in the range of one tenth to one half the rate which would normally be recommended for use of the particular active ingredient. Thus if the active ingredient would normally give good control of the pest when applied at rates of from 0.01 to 0.2 lbs/acre, then the invention compositions may be used at rate (with respect to active ingredient) of from 0.001 to 0.1 lbs/acre.

The invention compositions and method are particularly useful in the control of lepidopterous pests of cotton, such as for example, larval forms of *Heliothis viriscens, Spodoptera littoralis* and the like.

The invention is further illustrated by the following Example.

EXAMPLE 1

This Example illustrates the compositions and methods of the invention, and compares an Ivermectin/"COAX" admixture with a cypermethrin/"COAX" mixture and with ivermectin and cypermethrin on their own in two tests, A and B.

The compound under test was dissolved in a mixture of acetone and ethanol (1:1 by volume) and aliquots taken and diluted either with deionised with water or with a 5000 parts per million solution of "COAX" to obtain compositions containing (for test A) 15.6, 7.8, 3.9, 1.95 and 0.98 parts per million and (for test B) 7.8, 3.9, 1.95, 0.98 and 0.49 parts per million of the compound.

These compositions were sprayed onto detached cotton leaves using a Potter tower and after drying the leaves were infested with 20 first instar larval *Heliothis viriscens.* Five replicates were used for each of the five rates of chemical used. The mortality of the pests was assessed after 48 hours and from the results the $LC_{50}$ and $LC_{90}$ values of each treatment determined. The results of two such tests are given in Tables I and II below. "COAX" alone at 5000 parts per million failed to provide any mortality.

From the results of the tests it can be seen that, when applied on their own cypermethrin and ivermectin are approximately equivalent in activity. "COAX" fails to enhance the activity of cypermethrin but does enhance the activity of ivermectin at the $LC_{50}$ level by a factor of from about 10 to 30, and at the $LC_{90}$ level by about 10 times.

TABLE I

| | Test A | | | |
|---|---|---|---|---|
| Treatment | $LC_{50}$ | Enhancement Ratio | $LC_{90}$ | Enhancement Ratio |
| Cypermethrin | 9.3 | 1.0 | 74.6 | 1.0 |
| Ivermectin | 8.3 | 1.1 (1.0) | 46.2 | 1.6 (1.0) |
| Ivermectin/ "COAX" | 0.27 | 34.4 (31.3) | 4.60 | 16.2 (10.1) |

TABLE II

| | Test B | | | |
|---|---|---|---|---|
| Treatment | $LC_{50}$ | Enhancement Ratio | $LC_{90}$ | Enhancement Ratio |
| Cypermethrin | 6.0 | 1.0 | 63.1 | 1.0 |
| Cypermethrin/ "COAX" | 6.1 | 0.97 | 138.6 | 0.46 |
| Ivermectin | 9.6 | 0.6 (1.0) | 45.3 | 1.4 (1.0) |
| Ivermectin/ "COAX" | 1.0 | 5.9 (9.8) | 5.0 | 12.7 (9.1) |

I claim:

1. A method for the control of insect pests of growing plants which comprises applying to the locus of the plant an insecticidally effective amount of an insecticidal composition comprising an insecticidally effective amount of a combination of at least one macrolide antibiotic substance selected from the group consisting of C-076 and B-41 antibiotics and acylated derivatives and aglycones thereof and an insect feeding stimulant containing one or more of cottonseed flour, disaccharide and vegetable lipid oil in association with an insecticidally inert diluent or carrier material.

2. A method according to claim 1 wherein the macrolide antibiotic is an avermectin.

3. A method according to claim 2 wherein the avermectin is avermectin $B_1a$ or the 22,23 dihydroderivative thereof.

4. A method according to claim 1 in which the rate of application with respect to the insect feeding stimulant is within the range 1 to 10 lbs/acre.

5. A method according to claim 1 wherein the pests are larval lepidopterous pests and the locus is a cotton crop.

* * * * *